(12) United States Patent
Dunko (10) Patent No.: US 8,519,835 B2
(45) Date of Patent: Aug. 27, 2013

(54) SYSTEMS AND METHODS FOR SENSORY FEEDBACK

(75) Inventor: Gregory A. Dunko, Cary, NC (US)

(73) Assignee: HTC Corporation, Taoyuan, Taoyuan County (TW)

( * ) Notice: Subject to any disclaimer, the term of this patent is extended or adjusted under 35 U.S.C. 154(b) by 373 days.

(21) Appl. No.: 13/038,620

(22) Filed: Mar. 2, 2011

(65) Prior Publication Data
US 2012/0223823 A1 Sep. 6, 2012

(51) Int. Cl.
*H04B 3/36* (2006.01)

(52) U.S. Cl.
USPC ...... 340/407.1; 340/506; 340/3.1; 340/539.1; 340/539.11

(58) Field of Classification Search
USPC ................ 340/407.1, 506, 3.1, 539.1, 539.11
See application file for complete search history.

(56) References Cited

U.S. PATENT DOCUMENTS

| | | | |
|---|---|---|---|
| 8,322,863 B1* | 12/2012 | Cho et al. | 353/70 |
| 2004/0143730 A1* | 7/2004 | Wen et al. | 713/150 |
| 2007/0120834 A1* | 5/2007 | Boillot | 345/173 |
| 2009/0177452 A1* | 7/2009 | Ullrich et al. | 703/11 |
| 2010/0153453 A1* | 6/2010 | Knowles | 707/784 |
| 2011/0066003 A1* | 3/2011 | Duffy | 600/300 |
| 2013/0110617 A1* | 5/2013 | Phan et al. | 705/14.43 |

* cited by examiner

*Primary Examiner* — Daryl Pope
(74) *Attorney, Agent, or Firm* — McClure, Qualey & Rodack, LLP (57) ABSTRACT

A sensory feedback system is described that comprises a sensor for measuring one or more physical attributes associated with a user and a mobile device coupled to the sensor, where the mobile device comprises a data capture device for receiving and storing measurements by the sensor. The mobile device is further configured to generate data according to the received measurements. The mobile device also comprises a data transceiver configured to transmit the generated data. The system further comprises a remote monitor communicatively coupled to the mobile device, where the remote monitor comprises a data processor configured to receive the data generated by the mobile device and generate one or more sensory response signals according to the received data generated by the mobile device.

21 Claims, 7 Drawing Sheets

SYSTEMS AND METHODS FOR SENSORY FEEDBACK

TECHNICAL FIELD

The present disclosure generally relates to systems and methods for providing sensory feedback.

BACKGROUND

Over the years, portable handheld devices such as smartphones have become prevalent. With the rapid development in communication technology, smartphones have become an integral part of many people's lives given the portability of smartphones, the convenient access to the Internet, and the growing number of applications available on smartphones. With the wide popularity of social networking, communities of users stay connected through the Internet. While many applications allow users to share and receive information, one perceived shortcoming with such applications is that the means of interaction is generally limited to reading and posting of text, images, videos, and other forms of media. A desire exists for an alternative means for enhanced or alternative social networking.

SUMMARY

Briefly described, one embodiment, among others, is a sensory feedback system that comprises a sensor for measuring one or more physical attributes associated with a user and a mobile device coupled to the sensor, where the mobile device comprises a data capture device for receiving and storing measurements by the sensor. The mobile device is further configured to generate data according to the received measurements. The mobile device also comprises a data transceiver configured to transmit the generated data. The system further comprises a remote monitor communicatively coupled to the mobile device, where the remote monitor comprises a data processor configured to receive the data generated by the mobile device and generate one or more sensory response signals according to the received data generated by the mobile device.

Another embodiment is a method for providing sensory feedback. The method comprises measuring, by a mobile device, one or more physical attributes associated with an individual and formatting the measured one or more physical attributes into data comprising a haptic representation of the measured one or more physical attributes. The method further comprises transmitting the data to a remote device and generating, by the remote device, sensory feedback according to the data received by the remote device, wherein the sensory feedback comprises one or more of: vibrations and light.

Another embodiment is a method that comprises measuring, by a mobile device, one or more physical attributes associated with an individual and formatting the measured one or more physical attributes into data comprising a haptic representation of the measured one or more physical attributes. The method further comprises transmitting the data to a plurality of remote devices according to respective permissions levels assigned to each of the plurality of remote devices and generating, by each of the plurality of remote devices, sensory feedback according to the received data, the sensory feedback comprising one or more of: vibrations and light.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Having summarized various aspects of the present disclosure, reference will now be made in detail to the description of the disclosure as illustrated in the drawings. While the disclosure will be described in connection with these drawings, there is no intent to limit it to the embodiment or embodiments disclosed herein. Rather, the intent is to cover all alternatives, modifications and equivalents included within the spirit and scope of the disclosure as defined by the appended claims.

With the ever-increasing popularity of social networking, communities of users stay connected through the Internet on their portable handheld devices. As described above, one perceived shortcoming with existing applications for networking is that the means of interaction is generally limited to reading and posting text, images, videos, and other forms of media. Various embodiments are described for providing an alternative means of social networking whereby a community of users can "feel" what a particular individual is feeling or experiencing.

The sensory feedback systems and methods described may be used in a wide range of applications. One example application is sports and fitness activities. Currently, there are ongoing concept studies for developing smartphones that can be worn during sports and fitness related activities. For example, smartphones may be used for such fitness activities as jogging, bicycling, etc. For various embodiments, a sensor is coupled to a wearable device via, for example, a wireless connection, where the device captures such metrics as heart rate, blood pressure, $VO_2$ (maximized oxygen consumption), body temperature, etc. These metrics are captured and processed in the handheld device for both immediate use (e.g., for displaying the metrics to the user) and for later use (e.g., for data analysis for trending purposes).

In accordance with exemplary embodiments, the use of sensory feedback provides interaction between the user wearing or carrying the handheld device and one or more remote users where the remote users receive sensory feedback such as vibrations generated by a local haptic device that simulates measurements relating to the individual being monitored. The use of sensory feedback in accordance with various embodiments may be implemented in conjunction with a number of devices such as vibrating battery packs, piezoelectric devices, LED flashes, and so on. Through the use of an "always connected" wearable mobile device, an active user is able to comfortably wear a device such as a handheld smartphone that is connected via a wireless connection and transmit real-time data\telemetry to a remote user.

Figure 1:
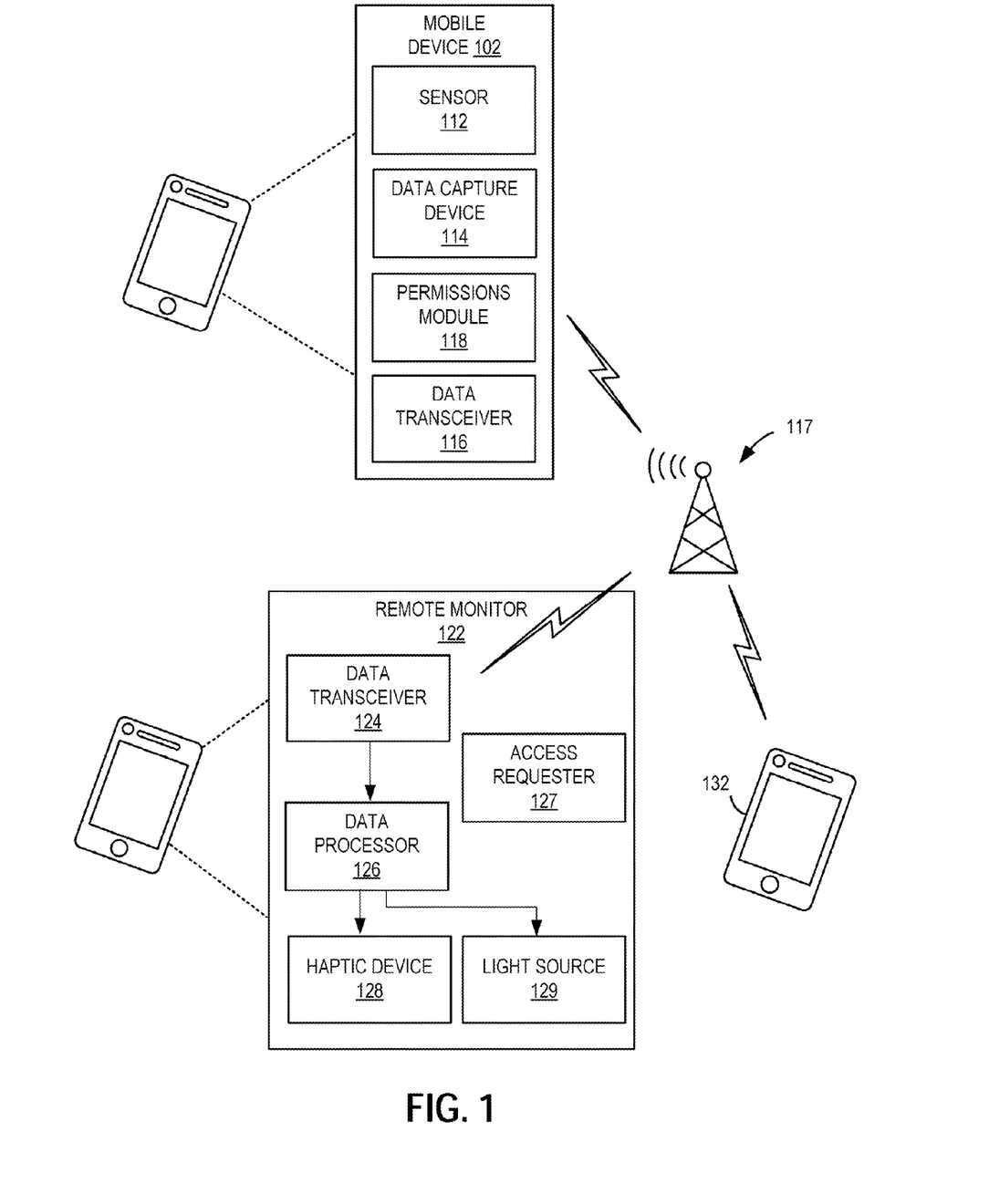
FIG. 1 is a block diagram of a mobile device configured to transmit data based on a user's activities.

A description of a system for providing sensory feedback in a networked environment is now described followed by a discussion of the operation of the components within the system. FIG. 1 is a block diagram of a mobile device 102 configured to transmit data based on a user's activities. The mobile device 102 may be embodied as a mobile computing device 102, such as by of example and without limitation, a smartphone. The mobile device 102 is preferably small enough to be carried by the user or strapped onto the user and comprises a sensor 112 configured to take measurements related to physical attributes of the user wearing the mobile device 102. The measurements may comprise, for example, heart rate, blood pressure, $VO_2$ (maximized oxygen consumption), body temperature, etc.

To further illustrate, the rhythmic beating of the user's heart or a change in body temperature may be detected by the sensor 112. Other examples include measurement of the systolic pressure over the diastolic pressure representing the individual's blood pressure. The data capture device 114 interfaces with the sensor 112 and logs data representing the measurements relating to the physical attributes. The data capture device 114 converts the captured data (e.g., blood pressure) and converts the data into a haptic representation to be conveyed to one or more remote users 122, 132. For example, the user's heartbeat may be represented by pulses where the timing of the pulses mimic that of the user's heartbeat. As another example, the user's body temperature may be represented by pulses, where slow pulses represent body temperature readings that fall below a predetermined threshold and where fast pulses represent body temperature readings that exceed the predetermined threshold. As will be described in detail later, these pulses are then "felt" by remote users via vibrations generated locally.

The mobile device 102 worn by the user further comprises a data transceiver 116 configured to transmit data generated by the data capture device 114 to remote monitors 122, 132. As will be described in more detail below, the data transceiver 116 may be compatible with various means of wireless communications, including, for example, cellular communications and Wi-Fi communications. Note that the data transceiver 116 is also capable of receiving data from other users, thereby allowing the user of the mobile device 102 to receive feedback from remote users. As will be described in connection with FIG. 2, the mobile device 102 may also be communicatively coupled to the remote monitors 122, 132 via other types of networks as well.

The remote monitor 122 comprises a data transceiver 124 for interfacing with the data transceiver 116 of the mobile device 102 worn by the individual being monitored. The data transceiver 124 in the remote monitor receives data generated by the data capture device 114. A data processor 126 in the remote monitor 122 receives the data from the data transceiver 124 and generates control signals for the haptic device 128. The haptic device 128 generates one or more vibrations according to the control signals generated by the data processor 126. In accordance with some embodiments, the data processor 126 also generates control signals for a light source 129 implemented within the remote monitor 122.

The light source 129 may comprise, for example, an LED flash such as those equipped on many smartphones today. The control signal(s) may be used to cause the light source 129 to flash according to a particular interval or to turn on continuously. For example, both the haptic device 128 and the light source 129 may be enabled or turned on in a synchronous fashion. For some embodiments, the haptic device 128 and the light source 129 may be configured to convey different types of information. For example, the haptic device 128 may be configured to vibrate according to the monitored individual's heartbeat while the light source 129 may be configured to turn on only if the individual's heartbeat exceeds a predetermined threshold.

Note that while not shown in FIG. 1, other sensory output devices may also be controlled by the data processor 126 to provide a representation of the data measured by the sensor 112 in the mobile device 102. For example, an audio output device such as a speaker can be utilized to generate a thumping sound that represents the heartbeat rhythm measured by the mobile device 102. The remote monitor 122 can also control a heat source that heats up according to the monitored user's body temperature, mood, etc. In this regard, variations and modifications may be made to the embodiments described without departing from the principles of the present disclosure.

Figure 2:
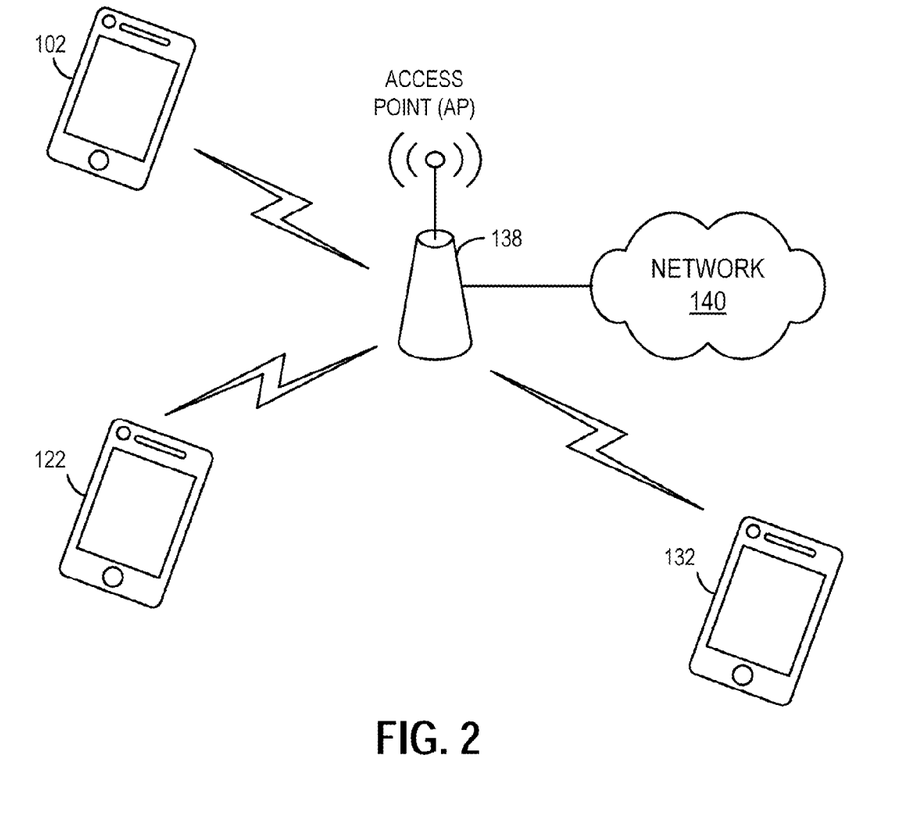
FIG. 2 depicts an alternative networked environment in which the various handheld devices in FIG. 1 may be communicatively coupled.

Reference is made to FIG. 2, which depicts an alternative networked environment in which the devices 102, 122, 132 shown in FIG. 1 may be coupled. As shown, the devices 102, 122, 132 may be part of an IEEE 802.11 network whereby the devices are wirelessly coupled to an access point 138, which provides access to a network 140 such as the Internet. The devices 102, 122, 132 may also be coupled via a Bluetooth connection or other wireless connection. Given the range provided by cellular networks, exemplary embodiments of the handheld devices 102, 122, 132 will generally communicate via cellular radio towers. However, the handheld devices 102, 122, 132 may also communicate via the wireless networks shown in FIG. 2 where cellular service is not available.

Figure 3:
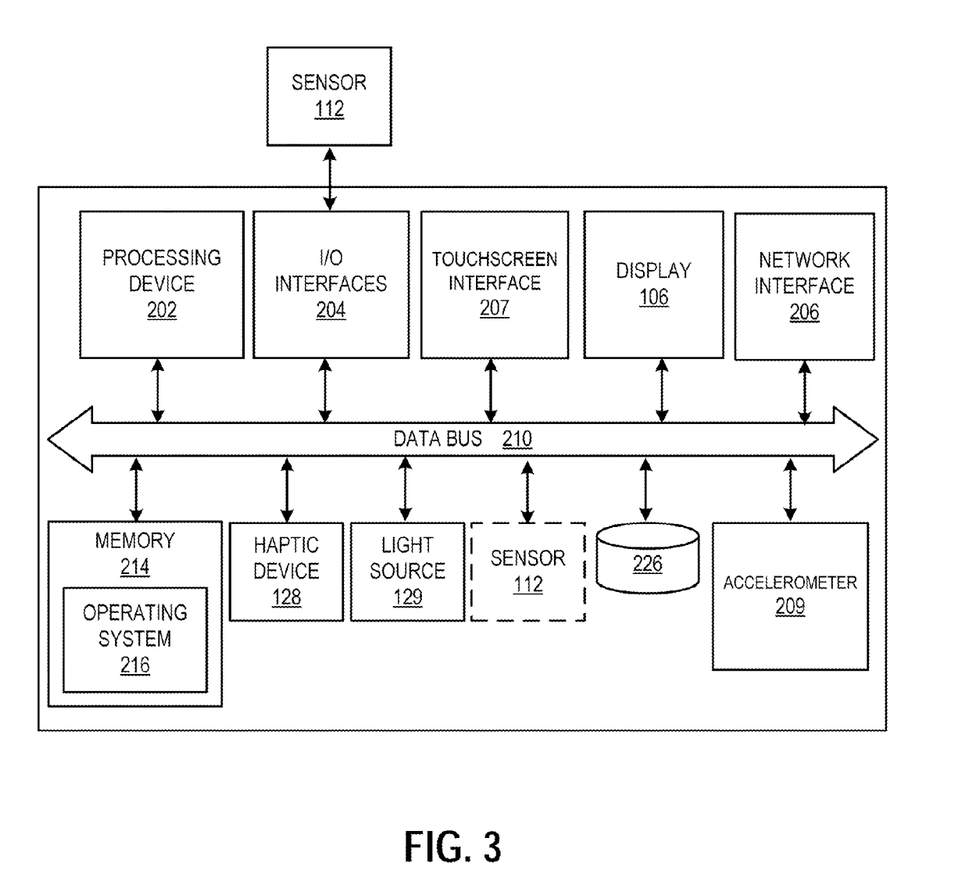
FIG. 3 illustrates an embodiment of the mobile device shown in FIG. 1.

FIG. 3 illustrates an embodiment of the mobile device 102 shown in FIG. 1. As described earlier, the mobile device 102 will typically be embodied as a smartphone but may also be embodied in any one of a wide variety of wired and/or wireless computing devices. As shown in FIG. 3, the mobile device 102 comprises memory 214, a processing device 202, a number of input/output interfaces 204, a network interface 206, a display 106, a touchscreen interface 207, an accelerometer 209, and mass storage 226, wherein each of these devices are connected across a local data bus 210. The mobile device 102 is configured to receive measurements via a sensor 112, which may be embodied as a separate device from the mobile device 102. For such embodiments, the sensor 112 may be coupled to the mobile device 102 via a wired or wireless connection, such as a USB connection via a USB, micro-USB, or mini-USB connector, a Bluetooth connection, and so on. Alternatively, the sensor 112 may be integrated as part of the mobile device 102. Note that while the haptic device 128 and light source 129 in FIG. 1 have been described in connection with the remote monitor 122, the mobile device 102 may also include these components. As such, FIG. 3 depicts the mobile device 102 as furthering comprising a haptic device 128 configured to provide tactile feedback. The mobile device 102 may further comprise a light source 129 such as an LED flash configured to not only illuminate objects but also to function as a visual indicator.

The processing device 202 may include any custom made or commercially available processor, a central processing unit (CPU) or an auxiliary processor among several processors associated with the mobile device 102, a semiconductor based microprocessor (in the form of a microchip), a macroprocessor, one or more application specific integrated circuits (ASICs), a plurality of suitably configured digital logic gates, and other well known electrical configurations comprising discrete elements both individually and in various combinations to coordinate the overall operation of the computing system.

The memory 214 can include any one of a combination of volatile memory elements (e.g., random-access memory (RAM, such as DRAM, and SRAM, etc.)) and nonvolatile memory elements. The memory 214 typically comprises a native operating system 216, one or more native applications, emulation systems, or emulated applications for any of a variety of operating systems and/or emulated hardware platforms, emulated operating systems, etc. For example, the applications may include application specific software which may comprise some or all the components of the mobile device 102 depicted in FIG. 1. In accordance with such embodiments, the components are stored in memory 214 and executed by the processing device 202.

The touchscreen interface 207 is configured to detect contact within the display area of the display 106 and provides such functionality as on-screen buttons, menus, keyboards, etc. that allow users to navigate user interfaces by touch. For some embodiments, the sensor 112 may comprise a touch pad or trackpad type device for detecting taps or scratches by the user that occur outside the touchscreen area. The sensor 112 translates or maps the motion and position of the user's finger to a particular function or input. For some embodiments, the mobile device 102 further comprises an accelerometer 209 configured to detect motion and vibration of the mobile device 102. The accelerometer 209 may be used in conjunction with the sensor 112 to obtain measurements based on movement by the user.

One of ordinary skill in the art will appreciate that the memory 214 can, and typically will, comprise other components which have been omitted for purposes of brevity. Note that in the context of this disclosure, a non-transitory computer-readable medium stores programs for use by or in connection with an instruction execution system, apparatus, or device. With further reference to FIG. 3, network interface device 206 comprises various components used to transmit and/or receive data over a networked environment such as the ones depicted in FIGS. 1 and 2. The remote monitors 122, 132 depicted in FIG. 1 may comprise similar components as those described above in connection with the mobile device 102. When such components as the data processor 126 in the remote monitor 122 are embodied as an application, the one or more components are stored on a non-transitory computer-readable medium and executed by the processing device.

Figure 4:
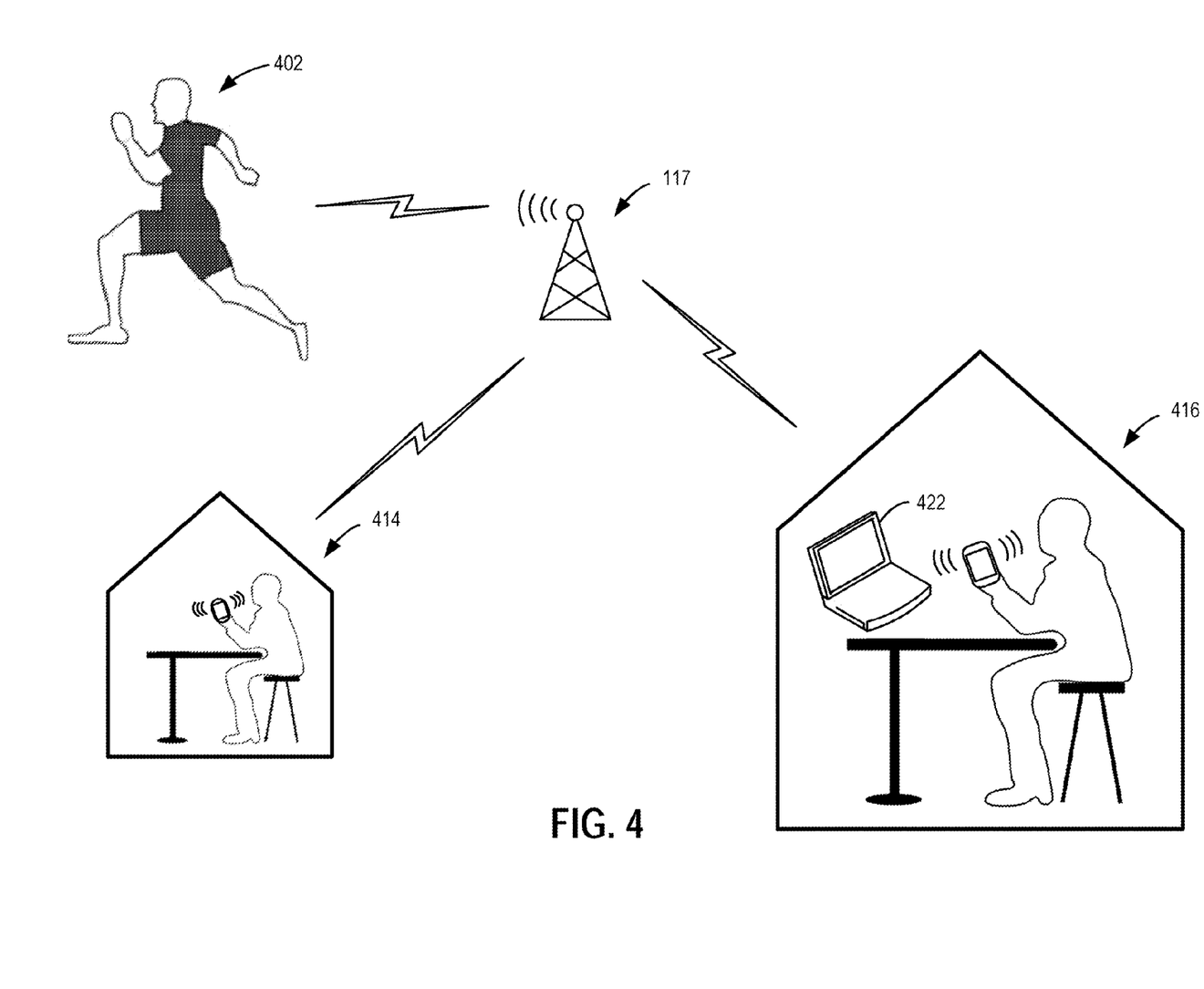
FIG. 4 illustrates an example application of the feedback system in FIG. 1.

Having described the basic framework and structure of the mobile device 102 and remote monitors 122, 132, an example application is now described in order to illustrate features of various embodiments. Reference is made to FIG. 4, which illustrates how multiple individuals can monitor and stay in contact with an individual. A first individual 402 is shown jogging. The individual 402 is wearing or carrying the mobile device 102 described in connection with FIG. 1. The mobile device 102 collects such data as the individual's 402 heartbeat, temperature, $VO_2$ level, and so on. Using the mobile device 102, the individual 402 transmit data via mobile communications through a cellular tower 117.

At two remote locations, individuals 414, 416 monitor the activities of the first individual 402 by receiving telemetering information from the first individual 402. Specifically, the respective monitor devices of the individuals 414, 416 generate sensory outputs for the individuals 414, 416 to follow what the first individual 402 is experiencing. For example, the sensor on the first individual's 402 mobile device collects blood pressure and heart rate information. Measurements are processed by the data capture device 114 (in FIG. 1) and transmitted via the data transceiver 116 to the remote individuals 414, 416. The remote monitor devices 122, 132 of each respective individual 414, 416 receives the data at the data transceiver 124, and the data processor 126 generates one or more controls signals that are sent to a haptic device 128 and/or a light source 129 on each remote monitor 122. The haptic device 128 generates pulses, for example, that mimic the current heartbeat of the first individual 402. The light source on the remote monitor 129 turns on if the number of heartbeats per minute exceeds a predetermined threshold. Note that the "pulses" could in fact be haptically generated heartbeats (that actually feel like a heartbeat) of a representative frequency (heart rate) and amplitude (blood pressure). For some embodiments, a remote user 416 may also receive telemetering data from the first individual 402 on a laptop 422 or other computing device equipped with a haptic device and/or light source.

In accordance with some embodiments, the remote individuals 414, 416 can transmit information back to the individual 402 being monitored. For example, the remote individuals 414, 416 can send text, images, videos, etc. to the individual 402 in response to the received sensory feedback generated by the first individual 402. The remote individuals 414, 416 can also generate vibrations and/or flashing lights for the first individual 402 to feel or view (for example, reassurance or feedback to "slow down"). While the illustration in FIG. 4 depicts two remote individuals 414, 416, more (or less) than two individuals can receive sensory feedback from the first individual 402 where a community of users can receive sensory feedback, thereby providing a different type social networking.

Figure 5:
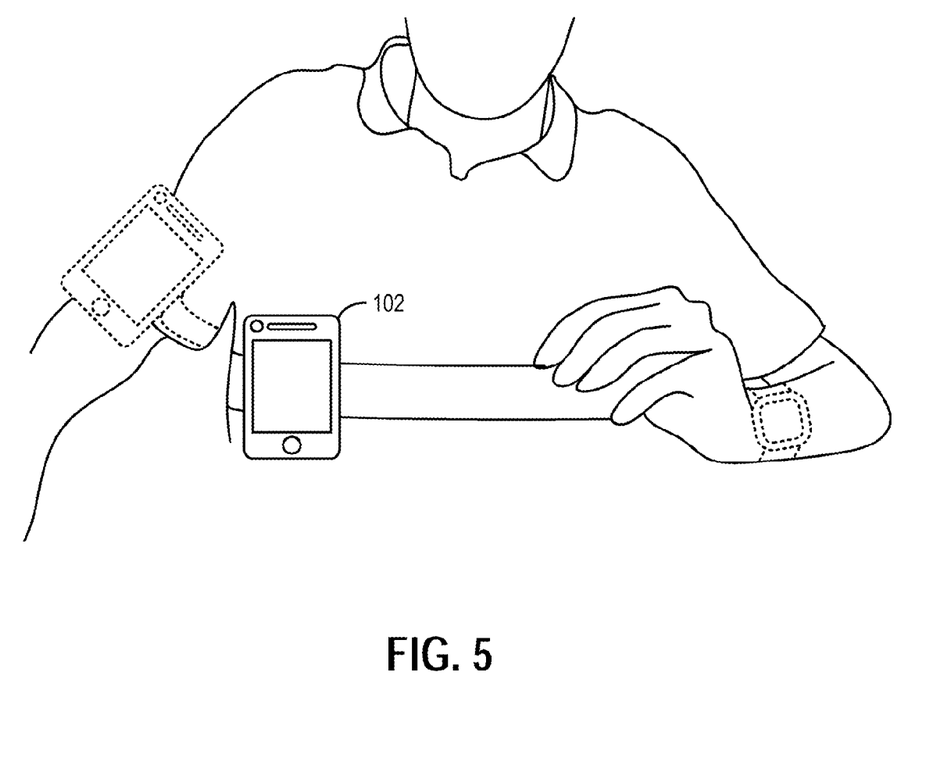
FIG. 5 depicts placement of the mobile device in FIG. 1 on an individual being monitored.

FIG. 5 depicts placement of the mobile device 102 in FIG. 1 on an individual being monitored. As shown, the mobile device 102 is worn or carried by an individual in a manner such that the mobile device 102 doesn't hinder the individual's activities. By way of example, the mobile device 102 may be attached to a harness worn around the chest area of the individual. Alternatively, the mobile device 102 can be worn around the individual's arm. For some embodiments, the mobile device 102 may even be worn around the individual's wrist. While not shown, the mobile device 102 may be coupled to an external sensor 112 (as described in connection with FIG. 3). The sensor 112 can be coupled to the mobile device 102 via a wireless connection such as a Bluetooth connection or ANT™ connection, where ANT™ is a wireless sensor network (WSN) radio frequency (RF) protocol used for low power networking applications. The sensor 112 may also be coupled to the mobile device via a wired connection such as a USB cable. Note that for some embodiments, the accelerometer 209 shown in FIG. 3 may be used to obtain measurements without the need for a separate sensor 112. In other embodiments, the accelerometer 209 may be used in conjunction with the sensor 112 to obtain measurements.

Figure 6A:
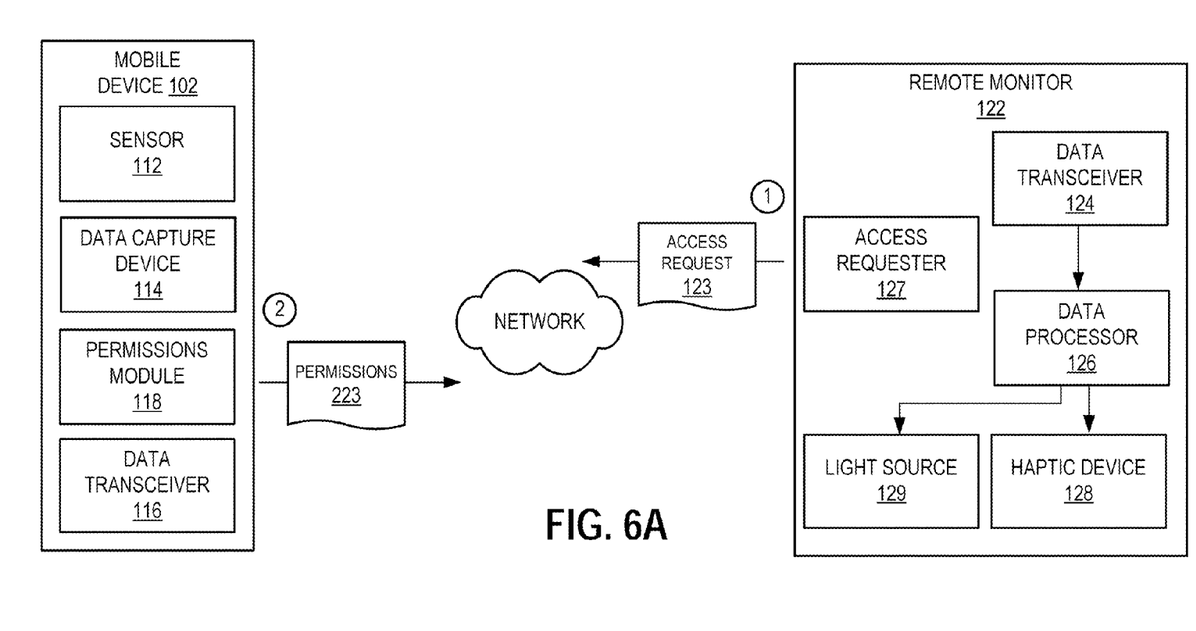
FIGS. 6A-6B depict how permissions are granted by the mobile device of FIG. 1 to one or more remote monitors.
Figure 6B:
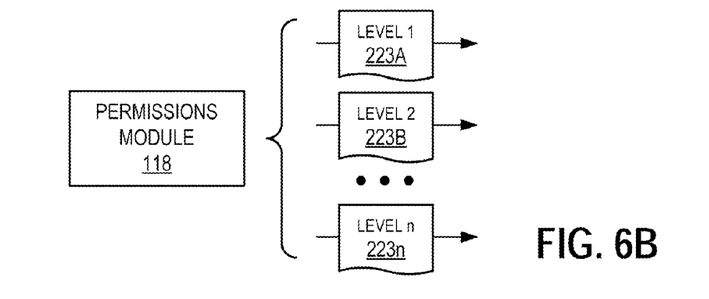

Reference is made to FIGS. 6A-6B, which depict how the user being monitored can control data access by remote users. In accordance with some embodiments, permissions levels are granted by the mobile device of FIG. 1 to one or more remote monitors. Rather than simply broadcasting telemetering data, a user can elect to limit access to the user's data to certain users, namely, friends, colleagues, etc., thereby creating a network or community of users that follow the user's activities. As shown in FIG. 6A, an access requester 127 in the remote monitor generates a request 123 and sends the request 123 to the mobile device 102. In response, a permissions module 118 in the mobile device 102 defines the permissions level for the remote monitor 122 and sends an acknowledgement 223. The acknowledgement 223 may define the permissions level granted to the remote monitor 122.

As shown in FIG. 6B, the mobile device 102 can individually define the permissions level of each remote user, where the different permission levels 223A, 223B, 223n correspond to different activities or different data to be monitored. For example, the user may elect to grant one remote user access to all data for all activities. For other remote users, the user may elect to grant limited access to certain activities, for example, sports and fitness activities. The permission levels 223A, 223B, 223n may also be defined according to time. For example, some remote users may be granted access twenty-four hours a day, whereas other remote users may be granted access for only one hour a day. In this regard, the user being monitored has full control over the data being transmitted to the community of users.

Figure 7:
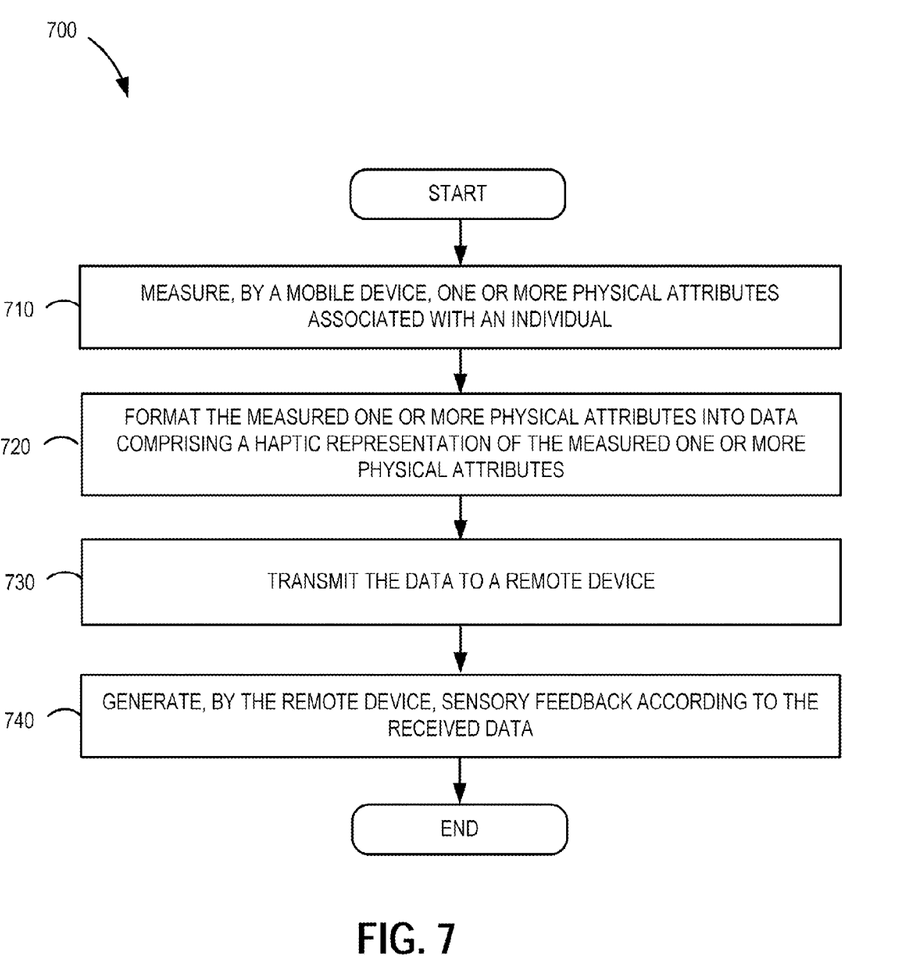
FIG. 7 is a flowchart for a method for providing sensory feedback utilizing the system shown in FIG. 1.

Reference is now made to FIG. 7, which is a flowchart 700 for a method for providing sensory feedback utilizing the devices shown in FIG. 1. If embodied in software, each block depicted in FIG. 7 represents a module, segment, or portion of code that comprises program instructions stored on a non-transitory computer readable medium to implement the specified logical function(s). In this regard, the program instructions may be embodied in the form of source code that comprises statements written in a programming language or machine code that comprises numerical instructions recognizable by a suitable execution system such as the mobile device 102 shown in FIG. 1. The machine code may be converted from the source code, etc. If embodied in hardware, each block may represent a circuit or a number of interconnected circuits to implement the specified logical function(s).

Although the flowchart 700 of FIG. 7 shows a specific order of execution, it is understood that the order of execution may differ from that which is depicted. In block 710, a mobile device measures one or more physical attributes associated with an individual. As described earlier, the physical attributes may include, but is not limited to, heat beat rate, heart pressure, VO$_2$ (maximized oxygen consumption) levels, and body temperature. In block 720, the measurements are formatted into data comprising a haptic representation of the measured physical attributes. For example, a haptic representation of a heartbeat rate may simply comprise vibrations that mimic the heartbeat rhythm. In block 730, the data is transmitted by the mobile device 102 to a remote device 122, such as the one depicted in FIG. 1. In block 740, the remote device 122 generates sensory feedback according to the received data.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

At least the following is claimed:
1. A sensory feedback system, comprising:
   a sensor for measuring one or more physical attributes associated with a user;
   a mobile device coupled to the sensor, the mobile device comprising:
      a data capture device for receiving and storing measurements by the sensor, the mobile device being further configured to generate data according to the received measurements;
      a data transceiver configured to transmit the generated data; and
   a remote monitor communicatively coupled to the mobile device, the remote monitor comprising a data processor configured to receive the data generated by the mobile device and generate one or more sensory response signals according to the received data generated by the mobile device.

2. The system of claim 1, wherein the remote monitor further comprises a haptic device configured to receive the one or more sensory response signals and generate vibrations according to the one or more sensory response signals.

3. The system of claim 2, wherein the vibrations generated by the haptic device comprise a haptic representation of the one or more measured physical attributes of the user.

4. The system of claim 3, wherein the haptic representation of the one or more measured physical attributes of the user comprise one or more of:
   haptically generated heartbeats at a frequency corresponding to heart rate of the user; and
   haptically generated heartbeats at an amplitude corresponding to blood pressure of the user.

5. The system of claim 1, wherein the remote monitor further comprises a light source configured to receive the one or more sensory response signals and to illuminate according to the one or more sensory response signals.

6. The system of claim 1, wherein the mobile device and the remote monitor comprise cellular telephones.

7. The system of claim 1, wherein the mobile device and the remote monitor are communicatively coupled via a cellular network.

8. The system of claim 1, wherein the mobile device and the remote monitor are communicatively coupled via an IEEE 802.11 based network.

9. The system of claim 1, wherein the remote monitor further comprises an access requester configured to request data access from the mobile device.

10. The system of claim 9, wherein the mobile device further comprises a permissions module configured to grant a permissions level in response to the data access request.

11. The system of claim 1, wherein the one or more physical attributes comprise one or more of: heat beat rate, heart pressure, VO$_2$ (maximized oxygen consumption) levels, and body temperature.

12. A method for providing sensory feedback, comprising:
   measuring, by a mobile device, one or more physical attributes associated with an individual;
   formatting the measured one or more physical attributes into data comprising a haptic representation of the measured one or more physical attributes;
   transmitting the data to a remote device; and
   generating, by the remote device, sensory feedback according to the data received by the remote device, wherein the sensory feedback comprises one or more of: vibrations and light.

13. The method of claim 12, wherein the sensory feedback comprises vibrations that track the one or more measured physical attributes.

14. The method of claim 12, further comprising requesting access, by the remote device, to the measured one or more physical attributes.

15. The method of claim 12, wherein the one or more physical attributes comprise one or more of: heat beat rate, heart pressure, VO$_2$ (maximized oxygen consumption) levels, and body temperature.

16. The method of claim 14, further comprising granting, by the mobile device, a permissions level in response to the request for access.

17. The method of claim 16, wherein the permissions level is defined according to one or more of activities and time.

18. A method for providing sensory feedback, comprising:
   measuring, by a mobile device, one or more physical attributes associated with an individual;
   formatting the measured one or more physical attributes into data comprising a haptic representation of the measured one or more physical attributes;
   transmitting the data to a plurality of remote devices according to respective permissions levels assigned to each of the plurality of remote devices; and
   generating, by each of the plurality of remote devices, sensory feedback according to the received data, the sensory feedback comprising one or more of: vibrations and light.

19. The method of claim 18, wherein the one or more physical attributes comprise one or more of: heat beat rate, heart pressure, VO$_2$ (maximized oxygen consumption) levels, and body temperature.

20. The method of claim 18, wherein the permissions levels are defined according to the one or more physical attributes.

21. The method of claim 18, wherein transmitting the data to a plurality of remote devices is performed over a cellular network.

* * * * *